United States Patent [19]

Dessau

[11] Patent Number: 4,666,874

[45] Date of Patent: May 19, 1987

[54] STEREODIFFERENTIATING HYDROCARBON CONVERSION ZEOLITE CATALYSTS

[75] Inventor: Ralph M. Dessau, Edison, N.J.

[73] Assignee: Mobil Oil Corporation, New York, N.Y.

[21] Appl. No.: 792,398

[22] Filed: Oct. 29, 1985

Related U.S. Application Data

[63] Continuation of Ser. No. 655,816, Oct. 1, 1984, Pat. No. 4,554,262.

[51] Int. Cl.$^4$ .......................... B01J 29/06; B01J 27/18
[52] U.S. Cl. ........................................ 502/62; 502/66; 502/74; 502/214
[58] Field of Search ...................... 502/62, 66, 74, 214

[56] References Cited

U.S. PATENT DOCUMENTS

| | | | |
|---|---|---|---|
| 2,736,689 | 2/1956 | Stuart | 502/62 X |
| 3,970,544 | 7/1976 | Rosinski et al. | 502/62 X |
| 4,213,921 | 7/1980 | Mitchell et al. | 502/62 X |
| 4,265,827 | 5/1981 | Knowles et al. | 260/440 |
| 4,273,933 | 6/1981 | Harada et al. | 560/179 |
| 4,554,262 | 11/1985 | Dessau | 502/62 |

OTHER PUBLICATIONS

Kirk–Othmer, Encyclopedia of Chemical Technology, Third Edition, vol. 17, pp. 311–345, Wiley–Interscience, New York, New York 1982.

Journal of Molecular Catalysis, 9 (1980), 381–387, "Asymmetric Hydrogenation of Substituted Acrylic Acids by Rh'-Aminophosphine Chiral Complex Supported on Mineral Clays", M. Mazzei, W. Marconi and M. Riocci.

Primary Examiner—Carl F. Dees
Attorney, Agent, or Firm—A. J. McKillop; M. G. Gilman; L. P. Hobbes

[57] ABSTRACT

A stereo-differentiating catalyst containing metal is prepared by contacting a metal-containing acidic molecular sieve material, such as a zeolite with an optically active base, such as amine. Methods are disclosed for utilizing the catalyst in hydrocarbon conversion processes, e.g., hydrogenation and hydroformylation.

16 Claims, No Drawings

STEREODIFFERENTIATING HYDROCARBON CONVERSION ZEOLITE CATALYSTS

This case is a continuation in part of U.S. application Ser. No. 655,816, filed Oct. 1, 1984 now U.S. Pat. No. 4,554,262.

Stereoisomers are chemical substances having the same molecular formula while differing in their arrangement of atoms in space. Enantiomers are stereoisomers which are mirror images of each other and which have the same physical and chemical properties except for their optical activity, i.e., an ability to rotate a plane of polarized light. Optically active dextrorotatory isomers (+ or d) rotate a plane of polarized light clockwise while levorotatory isomers (− or l) rotate the plane of light counterclockwise.

Addition of more than one asymmetric center into a molecule produces diastereomers that do not have the same chemical or physical properties. Diastereomers are stereoisomers that are not mirror images of each other.

Because the biological activities of many compounds are influenced by stereochemical factors it is often desirable to produce such optically active materials. However, special precautions must be taken to ensure production of an optically active product because of the tendency to produce optically inactive racemic mixtures, that is equal amounts of each mirror image stereoisomer whose opposite optical activities cancel out each other. For example, when an olefin, which in its saturated form is optically active, is hydrogenated, the usual resultant product is optically inactive due to formation of the racemic mixture. In order to obtain the desired enantiomer or mirror image stereoisomer, the mixture must be separated into its optically active components. This separation, known as optical resolution may be carried out by actual physical sorting or by direct crystallization of racemic mixtures. However, the most common form of optical resolution involves formation of diastereomeric derivatives by means of an optically active resolving agent. Because the resulting diastereomers, unlike enantiomers have different physical properties, they may be separated by various methods including fractional crystallization, gas-liquid chromatography, thin layer chromatography and liquid chromatography. However, such optical resolution procedures are often laborious, expensive as well as destructive to the undesired enantiomorph. Due to these difficulties, increased attention has been placed upon asymmetric synthesis in which one of the enantiomorphs is obtained in significantly greater amounts. In asymmetric synthesis an achiral unit in an ensemble of substrate molecules is converted by a reactant into a chiral unit in such a manner that the stereoisomeric products are produced in unequal amounts. A prochiral function serves as the precursor for a chiral product during the reaction. Further information relating to asymmetric synthesis may be found in Kirk-Othmer, Encyclopedia of Chemical Technology, Third Edition, Volume 17, pages 311–345, Wiley-Interscience, New York, N.Y., 1982, incorporated herein by reference.

Catalytic asymmetric catalysts are known in the art. For example, U.S. Pat. No. 4,265,827, discloses a process for the homogeneous catalytic hydrogenation of certain organic acids to produce an optically active mixture. Hydrogenation is carried out in the presence of an optically active coordinated metal complex hydrogenation catalyst in which the metal is selected from the group consisting of rhodium, iridium, ruthenium, osmium, palladium and platinum. Such catalysts are soluble in the reaction mixture and are known as "homogeneous" catalysts.

U.S. Pat. No. 4,273,933 discloses a modified nickel catalyst employed for stereo-diffentiating reduction of carbonyl compounds. The modified nickel catalyst is prepared by soaking a nickel catalyst in an aqueous modifying medium having dissolved therein an inorganic salt, and an optically active substance such as optically active hydroxy acid. The nickel catalyst may be supported on a conventional carrier, such as diatomaceous earth or alumina.

The present invention relates to a process for preparing asymmetric catalysts which comprises contacting an acidic molecular sieve material with an optically active organic base. Such bases may be defined for the purposes of the present invention as any optically active organic compounds capable of adsorption by or complexing with acidic sites and may include optically active amines, phosphines, alcohols, olefins, aromatics, esters, ketones, ethers, and acetylenes. Amines are especially preferred.

Acidic molecular sieve materials are inorganic oxide molecular sieve materials having acidic catalytic activity. Exemplary materials include catalytic activity such as the silicoaluminophosphates (SAPOs), e.g. SAPO-5 described in U.S. Pat. No. 4,440,871, or zeolites. Suitable zeolites include those shape-selective zeolites of intermediate pore size having Constraint Index values from about 1 to 12 as well as large pore size zeolites having a Constraint Index value less than about 1.

The catalysts prepared in accordance with the present invention are particularly suitable for preferentially converting one optical isomer relative to its enantiomer as well as the preferential formation of an optically active product from a non-chiral feed.

Asymmetric catalysts of the present invention may be prepared by incorporating a Group VIII metal into an acidic molecular sieve material, such as a zeolitic material, and if necessary, exposing the resulting metal-containing acidic molecular sieve material to reducing conditions so as to limit the susceptibility of the incorporated Group VIII metal to migration and agglomeration. Where metal has been incorporated into the material in a partially reduced state, e.g., $Rh^+$ in the form of rhodium carbonyl chloride, a reduction step is unnecessary. The metal-containing material is then reacted with a chiral or optically active amine in order to neutralize some of the acidic sites present. Group VIII metal is particularly preferred, especially for asymmetric hydrogenation catalysts. Other asymmetric syntheses to which the present zeolites are suited include asymmetric hydroformylation and asymmetric alkylation.

Zeolites are particularly useful acidic molecular sieve materials for use in the present invention and can be described as crystalline metallosilicates consisting of a rigid three dimensional framework of $SiO_4$ or an $MO_4$ where M is a Group III A metal, for example, aluminum or gallium, wherein the tetrahedra are cross-linked by the sharing of oxygen atoms such that the ratio of the total Group III A metal and silicon atoms to oxygen is 1:2. The electrovalence of the tetrahedra containing Group III A metal is balanced by the inclusion in the crystal of a cation, for example, an alkali metal or an alkaline earth metal cation. This can be expressed wherein the ratio of metal M to the number of various cations, such as Ca/2, Sr/2, Na, K or Li is equal to unity. One type of cation may be exchanged either entirely or partially by another type of cation utilizing ion exchange techniques in a conventional manner. By means of such cation exchange, it has been possible to vary the properties of a given zeolite by suitable selection of the cation.

Prior art techniques have resulted in the formation of a great variety of synthetic zeolites. These zeolites have come to be designated by letter or other convenient symbols, as illustrated by zeolite X (U.S. Pat. No. 2,882,244) zeolite Y (U.S. Pat. No. 3,130,007), ZK-5 (U.S. Pat. No. 3,247,195, ZK-4 (U.S. Pat. No. 3,314,752), zeolite beta (U.S. Pat. No. 3,308,069), ZSM-5/ZSM-11 intermediate compositions (U.S. Pat. No. 4,229,424), ZSM-5 (U.S. Pat. No. 3,702,886), ZSM-11 (U.S. Pat. No. 3,709,979), ZSM-12 (U.S. Pat. No. 3,832,449) ZSM-23 (U.S. Pat. No. 4,076,842), ZSM-35 (U.S. Pat. No. 4,016,245), ZMS-38 (U.S. Pat. No. 4,046,859) and ZSM-48 (U.S. Pat. No. 4,375,573), merely to name a few. All of the above patents are incorporated herein by reference.

Another suitable zeolite, ZSM-50 has a formula, on an anhydrous basis and in terms of moles of oxides per 100 moles of silica, as follows:

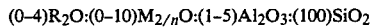

$$(0-4)R_2O:(0-10)M_{2/n}O:(1-5)Al_2O_3:(100)SiO_2$$

wherein M is an alkali or alkaline earth metal, n is the valence of M, and R is an organic cation of a Group VA element of the Periodic Table of the Elements (Sargent-Welch Scientific Company), particularly that derived from a linear diquaternary ammonium, phosphonium, arsonium, stibonium or bismuthonium compound having the general formula:

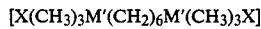

$$[X(CH_3)_3M'(CH_2)_6M'(CH_3)_3X]$$

wherein X is a halide anion (e.g. fluoride, chloride, bromide or iodide).

Catalytically active members of the family of the ZSM-50 crystals have a definite X-ray diffraction pattern which distinguishes them from other crystalline materials. The X-ray diffraction pattern of zeolite ZSM-50 has the following significant lines:

TABLE 1

| Interplanar d-Spacing (A) | Relative Intensity, I/Io |
|---|---|
| 20.1 ± .3 | W |
| 11.1 ± .17 | S |
| 10.1 ± .16 | M |
| 9.7 ± .14 | W |
| 5.77 ± .09 | W |
| 5.61 ± .09 | W |
| 4.64 ± .07 | M |
| 4.35 ± .07 | M |
| 4.30 ± .07 | VS |
| 4.00 ± .06 | S |
| 3.85 ± .06 | M |
| 3.70 ± .06 | M |
| 3.42 ± .05 | W |
| 3.35 ± .05 | W |
| 3.27 ± .05 | M |
| 3.24 ± .05 | W |
| 2.94 ± .04 | W |

TABLE 1-continued

| Interplanar d-Spacing (A) | Relative Intensity, I/Io |
|---|---|
| 2.53 ± .04 | W |

In Table I, the relative intensities are given in terms of the symbols W = weak, M = medium, S = strong and VS = very strong.
In terms of intensities, these may be generally designated as follows:
W = 0–20
M = 20–40
S = 40–60
VS = 60–100

ZSM-50 can be prepared from a reaction mixture containing sources of an alkali or alkaline earth metal oxide, an oxide of aluminum, an oxide of silicon, an organic cation of a Group VA element of the Periodic Table and water and having a composition, in terms of mole ratios of oxides, falling within the following ranges:

| Reactants | Useful | Preferred |
|---|---|---|
| $SiO_2/Al_2O_3$ | 20–100 | 30–90 |
| $OH^-/SiO_2$ | 0.1–0.6 | 0.1–0.3 |
| $R/SiO_2$ | 0.05–0.6 | 0.1–0.3 |
| $M/SiO_2$ | 0.01–1.0 | 0.1–0.6 | wherein R and M are as above defined.

The ZSM materials and zeolite beta noted above are shape-selective materials having a high silica content. These aluminosilicates have a silica to alumina mole ratio of at least 12, say about 70 or even about 100 or 200 or greater. Such materials also have a Constraint Index within the range of about 1–12. Methods for determination of Constraint Index are well-known and are set out in the Journal of Catalysis 67, 218–222 (1981).

The zeolites of the present invention may contain metals selected from the group consisting of Groups IB, IIB, IIIA, IIIB, IVA, IVB, VA, VB, VIA, VIB, VIIA and VIII of the Periodic Table. Zeolite containing Group VIII metal as a hydrogenating agent is particularly preferred. The metal can be added to the zeolite by conventional impregnation methods, which may include ion exchange. The metals may be incorporated within the zeolite by ion exchange by dissolving a metal or metal compound in a carrier liquid which is not only a good solvent for the desired metal complex but which also does not destroy the zeolite or where present, the zeolite binder. Preferred solvents are of molecular dimensions such that they can freely penetrate the pores of the zeolite selected. Between about 5 and 100% by weight, preferably between about 10 and 90% by weight of the original metal cations in the zeolite are exchanged with the solubilized or metal compound. Impregnation may be carried out by preparing an aqueous or organic solvent solution of the metal complex and contacting the zeolite preferably in the acidic form, with the solution at a temperature between the freezing point of the solvent and about 100° C., such that the resulting zeolite contains from about 0.1 to 10% by weight of metal, preferably about 0.1 to 1% by weight. Depending on its intended use, the zeolitic material upon removal from the contacting solution may be washed with a suitable solvent.

Representative ion exchange techniques are disclosed in a wide variety of patents, including U.S. Pat. No. 3,142,249; U.S. Pat. No. 3,142,251; and U.S. Pat. No. 3,140,253. These patents are incorporated herein by reference.

If necessary, after the metal incorporation step, the zeolite or other acidic molecular sieve material may be subjected to reducing conditions in order to reduce at least some of the metal incorporated within the molecular sieve material in such a way as to limit metal migration and agglomeration. Metal reduction can be accomplished by contacting the metal impregnated molecular sieve material with a suitable reducing agent such as hydrogen at temperatures ranging from about 20° to about 500° C., preferably about 300° to about 500°, and pressures ranging from about 1 to about 20 atm., preferably about 1 to about 10 atmospheres. In those cases where the molecular sieve material contains a form of platinum or palladium, it is preferred that the material be calcined by gradually increasing it from ambient temperature to about 350° C. in the presence of oxygen. The reducing agent may be combined with an inert diluent material such as nitrogen. The reduction process results in a metal containing molecular sieve containing acidic sites resulting from reduction of the metal cation, e.g., in the case of platinum tetramine loaded zeolites:
$H_2 + Pt(NH_3)_4 \rightarrow Pt° + 2H^+ + 4NH_3 \uparrow$.

After reduction, the metal-loaded acidic molecular sieve material is contacted with an optically active chiral Lewis base, e.g. an amine. Contacting conditions include temperatures ranging from about 100°–600° C., preferably about 300°–500° C. The optically active chiral bases suitable for use in the present invention are characterized by an ability to enter the pores of the molecular sieve material. Examples of the amines include S-(−)-alpha-methylbenzylamine or (S)-(−)-2-methylbutylamine, (S)-(+)-alanine, (S)-(+)-valine, and (R)-(−)valine. The acidic molecular sieve materials are contacted with the optically active organic base for a sufficient time to permit neutralization of some of the acidic sites. The amount of amine added should be such that it occupies about 20–50% of the pore volume of the molecular sieve material. The resulting optically active material may be further treated by combining it with a suitable inorganic matrix such as silica, alumina or silica-alumina.

The resulting product of the present invention is suitable for use in asymmetric catalysis as a stereo-differentiating hydrogenation catalyst. Such asymmetric catalysis may be used in the preferential conversion of one optical isomer relative to its enantiomer, in the preferential formation of an optically active product from a non-chiral feed, such as an optically active alcohol from a ketone, or in the hydroformylation of an olefinic material.

The invention can be further illustrated by the following examples which are to be understood as exemplifying specific embodiments of the present invention without limiting the same.

EXAMPLE 1

Preparation of Group VIII Metal Containing Zeolite treated with S-(−)-α-Methylbenzylamine As synthesized ZSM-5 is ion-exchanged with ammonium chloride to produce NH₄ZSM-5. NH₄ZSM-5 is then ion-exchanged with platinum by contact with a Pt+(NH₃)₄(NO₃)₂ solution overnight. The resulting material is elevated from room temperature to 350° C. in the presence of oxygen at a rate of about 0.5° C./minute. The calcined material is then reduced in the presence of hydrogen gas to form a zeolite which contains acidic sites. 10 g of the reduced acidic platinum-loaded product is contacted with 0.3 g of optically active S-(−)-alpha-methylbenzylamine dissolved in toluene to form a platinum loaded ZSM-5 zeolite having acid sites neutralized by the amine.

EXAMPLE 2

Conversion of 2-Phenylbutene To Optically Active 2-Phenylbutane

2-Phenylbutene is hydrogenated in the presence of the product of Example 1 and hydrogen under hydrogenation conditions. The reduction product, 2-phenylbutane exhibits optical activity.

EXAMPLE 3

Conversion of Acetylphenone To Optically Active 1-Phenylethanol

Acetophenone is contacted with hydrogen gas in the presence of the hydrogenation catalyst prepared in accordance with Example 1. Reduction is effected under conventional reduction conditions. The product of reduction is optically active 1-phenylethanol.

EXAMPLE 4

Preparation of Rhodium Hydroformylation Catalyst Containing Optically Active Amine As synthesized ZSM-5 is ion exchanged with ammonium chloride to produce NH₄ZSM-5, which is then treated with a solution of rhodium carbonyl chloride dimer in mesitylene.

10 g of the rhodium-loaded product is contacted with 0.3 g of optically active S-(−)-alpha-methylbenzylamine dissolved in toluene to form a rhodium loaded ZSM-5 zeolite having acid sites neutralized by the amine.

EXAMPLE 5

HYDROFORMYLATION OF α-METHYLSTYRENE

An autoclave is charged with 10 g of the catalyst of Example 4 and 50 g of α-methylstyrene. The contents of the autoclave are then heated to 100° C. and a 50/50 mixture of carbon monoxide and hydrogen is added to give a pressure of 1000 psig, which is maintained by periodic addition of the carbon monoxide-hydrogen mixture. After about 2 hours, the reaction mixture is withdrawn and found to contain optically active aldehydes.

What is claimed is:

1. A process for preparing an asymmetric synthesis catalyst which comprises contacting a metal-containing acidic molecular sieve material selected from the group consisting of zeolites and silicoaluminophosphates with an optically active Lewis base capable of adsorption by or complexing with acidic sites on said acidic molecular sieve material.

2. The process of claim 1 wherein said base is selected from the group consisting of phosphines, alcohols, olefins, aromatics, esters, ketones, ethers, and acetylenes.

3. The process of claim 1 wherein said metal is selected from the group consisting of Groups IB, IIB, IIIA, IIIB, IVA, IVB, VA, VB, VIA, VIB, VIIA and VIII of the Periodic Table.

4. The process of claim 1, wherein said metal is a Group VIII metal.

5. The process of claim 1 wherein said acidic molecular sieve material is a silicoaluminophosphate.

6. The process of claim 1 wherein said acidic molecular sieve material is a zeolite.

7. The process of claim 6 wherein said zeolite has a silica to alumina ratio of less than about 300 and a Constraint Index of less than about 12.

8. The process of claim 1 wherein said acidic molecular sieve material is a zeolite having a silica to alumina ratio of at least about 12 and a Constraint Index ranging from about 1 to 12.

9. The process of claim 4 wherein said Group VIII metal is selected from the group consisting of Pt, Pd, Ru and Rh.

10. The process of claim 6 wherein said zeolite is selected from the group consisting of zeolite X, zeolite Y and ZSM-20.

11. The process of claim 6 wherein said zeolite is selected from the group consisting of zeolite beta, ZSM-5, ZSM-5/ZSM-11 intermediate, ZSM-11, ZSM-12, ZSM-23, ZSM-35, ZSM-38, ZSM-48 and ZSM-50.

12. A process for preparing asymmetric hydrogenation catalysts which comprises incorporating a Group VIII metal into an acidic molecular sieve material selected from the group consisting of zeolites and silicoaluminophosphates and reacting said material with an optically active Lewis base capable of adsorption by or complexing with acidic sites on said acidic molecular sieve material.

13. The process of claim 12 wherein said acidic molecular sieve material is a zeolite.

14. The process of claim 13 wherein the metal-containing zeolite is exposed to reducing conditions prior to said reacting with an optically active Lewis base.

15. A chiral hydrogenating catalyst which is prepared by contacting a Group VIII-metal containing acidic molecular sieve material selected from the group consisting of zeolites and silicoaluminophosphates with an optically active Lewis base capable of adsorption by or complexing with acidic sites on said acidic molecular sieve material.

16. The catalyst of claim 15 wherein said molecular sieve material is a zeolite.

* * * * *